United States Patent [19]

Buchert

[11] Patent Number: 5,383,452
[45] Date of Patent: Jan. 24, 1995

[54] METHOD, APPARATUS AND PROCEDURE FOR NON-INVASIVE MONITORING BLOOD GLUCOSE BY MEASURING THE POLARIZATION RATIO OF BLOOD LUMINESCENCE

[76] Inventor: Janusz Buchert, 265 Cabrini Blvd., #6E, New York, N.Y. 10040

[21] Appl. No.: 86,236

[22] Filed: Jul. 1, 1993

[51] Int. Cl.⁶ .............................................. A61B 5/00
[52] U.S. Cl. .................... 128/633; 128/666; 128/653.1
[58] Field of Search ............ 128/633, 664–666, 128/653.1; 356/41

[56] References Cited

U.S. PATENT DOCUMENTS

| | | | |
|---|---|---|---|
| 3,958,560 | 5/1976 | March | 128/2 A |
| 3,963,019 | 6/1976 | Quandt | 128/2 T |
| 4,014,321 | 3/1977 | March | 128/2 A |
| 4,498,774 | 2/1985 | Yeung | 356/368 |
| 4,901,728 | 2/1990 | Hutchison | 128/633 |
| 5,009,230 | 4/1991 | Hutchinson | 128/633 |
| 5,068,536 | 11/1991 | Rosenthal | 250/341 |
| 5,070,874 | 12/1991 | Barnes et al. | 128/633 |
| 5,099,841 | 3/1992 | Heinonen | 128/633 |
| 5,115,137 | 5/1992 | Anderson-Engels | 250/461.2 |
| 5,127,406 | 7/1992 | Yamaguchi | 128/633 |
| 5,137,023 | 8/1992 | Mendelson | 128/633 |
| 5,183,042 | 2/1993 | Harjunmaa | 128/633 |
| 5,204,532 | 4/1993 | Rosenthal | 250/633 |
| 5,209,231 | 5/1993 | Cote | 128/633 |
| 5,222,496 | 6/1993 | Clarke | 128/633 |
| 5,243,983 | 9/1993 | Tarr et al. | 128/633 |

*Primary Examiner*—Lee S. Cohen
*Assistant Examiner*—Robert Nasser, Jr.

[57] ABSTRACT

A method, apparatus and procedure for the non-invasive detection of the sugar concentration changes in body liquids such as blood is disclosed. The instrument measures sugar concentration changes using the natural fingerprint of sugar which is rotations of polarization of light emitted from the biological particle chromophores dissolved together with sugar in human liquids. The degree of polarization of light emitted from luminescence centers undergoing interaction with an optically active medium such as sugar is proportional to the concentration of sugar in, for example, blood. The reference level is determined by conventional blood analysis using standard monitoring equipment during the special procedure of the Glucose Tolerance Test.

8 Claims, 4 Drawing Sheets

METHOD, APPARATUS AND PROCEDURE FOR NON-INVASIVE MONITORING BLOOD GLUCOSE BY MEASURING THE POLARIZATION RATIO OF BLOOD LUMINESCENCE

BACKGROUND OF THE INVENTION

1. Field of the invention

The present invention relates to a spectroscopic method for measuring the concentration changes of sugar and its derivatives in body liquids, for example in blood, using a non-invasive technique which does not require taking a sugar medium as a sample from the body for examination, and more particularly to a method and apparatus for detecting the polarization ratio of native emission of luminescence centers in a visible and/or near infrared region of spectrum from body liquid chromophores undergoing interaction with an optically active medium such as sugar.

2. Related art

The current state of the art in measuring sugar levels in body liquids or other objects such as foods, fruits and other agricultural products requires taking a sample from the object during the examination process. Special instruments are available for the purpose of determining blood glucose levels in people with diabetes. The technology uses a small blood sample obtained from a finger prick which is placed on chemically prepared strips and inserted into a portable instrument. The instrument analyzes the blood sample and provides a blood glucose level measurement. Diabetics must prick their fingers, sometimes up to four times a day, to draw blood for monitoring their glucose levels.

To eliminate the pain of drawing blood, as well as to eliminate a source of potential infection, non-invasive optical methods for sugar determination were invented and use absorption, transmission or reflection methods for spectroscopically analyzing blood glucose concentration.

In U.S. Pat. Nos. 3,958,560 and U.S. Pat. No. 4,014,321 to W. F. March, a unique glucose sensor to determine the glucose level in patients is described. The patient's eye is automatically scanned using a dual source of polarized radiation, each transmitting in different wavelengths at one side of the cornea of the patient. A sensor located at the other side of the cornea detects the optical rotation of the radiation that passed through the cornea. Because the level of glucose in the bloodstream of the patient is a function (not a simple one) of the glucose level in the cornea, rotation of polarization can determine the level of glucose concentration.

In U.S. Pat. No. 3,963,019 to R. S. Quandt there is described a method and apparatus for detecting changes in body chemistry, for example, glycemia, in which a beam of light is projected into and through the aqueous humor of the patient's eye. An analyzer positioned to detect the beam on its exit from the patient's eye compares the effect the aqueous humor has on said beam against a norm. The change in the glucose concentration is indicated and detected.

In U.S. Pat. No. 4,750,830 to A. St. J. Lee there is described a method of measuring the optical power of the living subject's eye and comparing it with a calibration value that corresponds to a reference blood glucose level. Optical power of the eye increases with blood glucose levels.

In U.S. Pat. No. 4,805,623 to F. Jobsis there is described a spectrophotometric method of qualitatively determining the concentration of a dilute component with a reference component of known concentration by a series of contemporaneous radiation-directing and measurements steps of radiation of selected varying wavelengths.

In U.S. Pat. No. 4,882,492 to K. J. Schlager there is described a non-invasive apparatus and related method for measuring the concentration of glucose or other blood analytes. It utilizes both diffuse reflected and transmissive infrared absorption measurements. The apparatus and method utilize non-dispersive correlation spectrometry. Differencing the light intensity between the two lights paths, one with a negative correlation filter and the other without, the apparatus provides a measure proportional to analyte concentration.

In U.S. Pat. No. 4,883,953 to K. Koashi and H. Yokota there is disclosed a method for measuring the concentration of sugar in liquids by use of near infrared light. The concentration of the sugar in the sample is determined by computing the absorption spectrum of the sugar at a different depth in the sample measured by a relatively weak power of infrared light, penetrating close to the surface in a sample, and a relatively strong power of infrared light penetrating relatively deeply in the sample.

In U.S. Pat. No. 5,009,230 to D. P. Hutchinson there is disclosed a device for the non-invasive determination of blood glucose in a patient. This glucose monitor is based upon the effect of glucose in rotating polarized infrared light. More specifically, two orthogonal and equally polarized states of infrared light of minimal absorption are passed through a tissue containing blood, and an accurate determination of change in signal intensity is made due to the angle of rotation of these states. This rotation depends upon the glucose level. This method uses transmission of infrared light through the tissue at minimum absorption of the tissue.

In U.S. Pat. Nos. 5,028,787 and 5,068,536 to R. D. Rosenthal at al. there is disclosed a near-infrared quantitative analysis instrument and method of calibration for non-invasive measures of blood glucose by analyzing near-infrared energy following interactance with venous or arterial blood, or transmission through a blood contained in a body part.

In U.S. Pat. No. 5,054,487 to R. H. Clarke there is disclosed a methods for non-invasive material analysis, in which a material is illuminated at a plurality of discrete wavelengths. Measurements of the intensity of reflected light at such wavelengths are taken, and an analysis of reflection ratios for various wavelengths are correlated with specific material properties such as concentration of analytes.

Other patents for non-invasively analyzing glucose levels in blood based on different spectroscopic, electrochemical and acoustic velocity measurement methods are as follows:

In U.S. Pat. Nos. 4,875,486 and 5,072,732 to U. Rapoport at al. there is disclosed a nuclear magnetic resonance apparatus, where predetermined water and glucose peaks are compared with the measured water and glucose peaks for determining the measured concentration.

In U.S. Pat. No. 5,056,521 to J. S. Parsons at al. there is disclosed a method in which a sample of specially collected oral fluid is placed into a monitoring instrument which generates an electrical glucose representative readout for oral fluid or whole blood.

In U.S. Pat. No. 5,119,819 to G. H. Thomas at al. there is disclosed acoustic velocity measurements for monitoring the effect of glucose concentration upon the density and adiabatic compressibility of serum.

In U.S. Pat. No. 5,139,023 to T. H. Stanley at al. there is disclosed a method for non-invasive blood glucose monitoring by correlating the amount of glucose which permeates an epithelial membrane, such as skin, with a glucose receiving medium over a specified time period. The glucose receiving medium is then removed and analyzed for the presence of glucose using conventional analytical technique.

In U.S. Pat. No. 5,140,985 to J. M. Schroeder at al. there is disclosed a measuring instrument and indicating device which gives an indication of blood glucose by metering the glucose content in sweat, or other body fluids, using a plurality of oxygen sensors covered by a semi-porous membrane. The device can be directly attached to the arm and the measuring device will react with localized sweating and indicate the wearer's blood glucose level.

The above described state of the art in non-invasive blood glucose measurements devices contains many approaches and indicates the importance of the problem. But none of the described devices have yet been marketed. Some inventors claim that instruments which are being developed give accurate blood glucose level readings and can be used for home testing by diabetics. They have limitations stemming from the use of near infrared light for measurement of absorption, transmission or reflectance; in this region of spectrum one can observe interference in absorption from other chemical components. Analyses based on only one or two wavelengths can be inaccurate if there is alcohol in the blood or any other substances that absorb at the same frequencies. In addition, these analyses can be thrown off by instrument errors, outlier samples (samples with spectra that differ from the calibration set) physiological differences between people (skin pigmentation, thickness of the finger). Methods of near infrared spectroscopy must be coupled with sophisticated mathematical and statistical techniques to distinguish between nonglucose sources and to extract a faint glucose spectral signature. Another limitation of these types of blood glucose testers is that they have to be custom calibrated for each user. The need for individual calibration results from the different combination of water levels, fat levels and protein levels in various people which cause changes in the absorption of near infrared light. Since the amount of glucose in the body is less than one thousandth that of other chemicals (and all of them possess absorption in the near infrared), variations of these constituents which exist among people may make universal calibration unlikely.

Other, non-invasive but also non-direct methods and instruments attempt to determine blood glucose content by measuring the glucose in sweat, saliva, urine or tears. These measurements, which can be quite reliable from the chemical analysis point of view, do not determine blood glucose levels because of the complicated, and not always well-defined, relation between blood glucose levels and glucose concentration in other body fluids. Other invented methods like acoustic velocity measurements in blood, are not very reliable because of the lack of well established and simple relations with blood glucose levels.

SUMMARY OF THE INVENTION

It is a principal object of the present invention to provide an apparatus and methods for glucose concentration measurements which can analyze the natural fingerprints of glucose: the state of rotations of polarization of native luminescence of the tissue.

It is the further object of the present invention to provide an instrument for glucose concentration determination. The said instrument externally measures the rotation of polarization of light emitted from luminescing centers of blood which are dissolved and/or attached to optically active molecules of sugar and, undergoing interaction, rotate the initial polarization.

It is still the further object of the present invention to provide the glucose level determination by detection method of emitted light from human tissue using electronic detection discrimination technique which can distinguish between blood and other tissues. It relies on the cardiac cycle of blood motion in the body. Detection is synchronized with the frequency of the patient's heart beat.

It is yet still further object of this invention to provide a technique for detecting the presence of other optically active molecules, as well as, of emitting molecules in the human body by means of measurements of polarization rotation of the light emitted by naturally emitting centers in blood or in other tissue, utilizing the synchronization to the heart beat technique for discriminatory detection, and to differentiate between blood molecules and other tissues as well as to subtract blood interference in measurement of molecules from other tissue in vivo.

It is another object of this invention to provide calibration of the ratio of light polarization changes or light polarization changes themselves to blood glucose concentration during the Glucose Tolerance Test performed, under medical supervision, where the whole range of glucose concentration levels are obtained and are linearly interpolated with the value of glucose measurement by conventional means.

The present inventions are based on the discovery that native visible and near infrared luminescence spectra from blood chromophores are substantially changed by means of light polarization rotation depending on the concentration of sugar in the blood; the luminescence signal is modulated by the frequency of the heart rate.

Due to its chemical structure glucose rotates the angle of transmitted polarized light. For example, D(+) Glucose (dextrose) (M. W. 180.16) solution in water with concentration c=10 [g/100 cm$^3$] has the specific rotation of $a_D = +53°$ (rotating clockwise). This feature is one of the most dramatic and differentiates this component from any others in blood. Some other organic components of blood or human tissue also possess optical activity which cannot be excluded. It will be measured as a constant background in comparison to the varying level of glucose in individual diabetic patients.

The light emitted from chromophores undergoing excitation by linearly or circularly polarized light has a polarization ratio corresponding to the optical activity of the chromophores themselves because other components of the tissue, except for the ones that are optically active, are interacting as isotropic mediums do. Optically active molecules in blood except sugar will create in measurements a constant background assuming a constant number of emitting centers. This constant background ratio of polarization rotation will be additionally modulated by optically active sugar molecules the concentrations of which are changing during the metabolic processes. These are the changes that interest us and are measured by our apparatus.

Our apparatus will measure not only the concentration of sugar molecules attached to the red blood cells but also concentration of sugar molecules which are not attached to red blood cells. In a normal person, blood contains about 5 to 6 percent of red cells attached to sugar molecules; the amount shifts very little. The percentage of red blood cells of diabetics attached to sugar molecules ranges from 7 to 13 percent or even higher. The emitted photons from chromophores of, for example, red blood cells will additionally pass through the optically active medium due to sugar content. Detecting only native luminescence light, emitted from the blood undergoing excitation in the main blood absorption band centered at about 420 nm, our instrument has an increased signal to noise ratio for the polarization rotation ratio measurements in comparison to polarization rotation measurements of transmitted or reflected light through the tissue. In the transmission and reflection of the light, light interacts and is scattered by all the molecules along the optical path of interaction in tissue. In our approach photons are emitted from, for example, red blood cell molecules (discriminated by detection wavelength) and the signal is proportional to the ratio of the red blood cell molecules to the optically active molecules. Further changes in the signal are proportional to the ratio of the red blood cells to the changes in the number of sugar molecules due to their concentration changes. This signal is directly proportional to the changes of blood glucose level.

To further increase the signal to noise ratio in the polarization ratio of native luminescence measurements our apparatus is using a discriminatory detection technique which can distinguish between blood and other tissue in the human body. It is based on the discovery that a luminescence signal from blood tissue is modulated by the frequency of the heart rate. The technique relies on the synchronous amplification of the electrical signal in phase with the cardiac cycle of blood motion in the body. It detects at the frequency equal to the heart beat. The luminescence signal is detected by a photomultiplier or a photodiode and amplified by an integrated circuits amplifier with a band pass filter allowing amplification only of AC (alternating current) band frequency signal in the range of heart rate. An AC signal of luminescence with frequency of heart rate is emitted only by tissue under constant motion in the body - the blood. The signal contains spectral information only about the chemical substances in the blood and not in bloodless tissue. This technique allows our instrument to extract and discriminate spectral information from tissue in motion which, in this case, is blood. This modulation, with frequency in the range of heart rate will be discriminated by a band pass electronic filter and amplified by a lock-in amplifier for the detection of the polarization ratio.

Changes of luminescence light rotation of polarization in the value of, for example, one-tenth part of degree will be measured using Glan-Thompson prism Polarizers made of two cemented calcite elements whose optical axis are parallel to the hypotenuse as well as to the entrance and exit faces. A characteristic parameter which allows measurements of such small angle rotations is the extinction ratio. The extinction ratio of this type of polarizer is in the range of $10^{-6}$ and for special quality prisms can reach the level of $10^{-8}$. However, by carefully selecting particular crystals and localized regions therein which are free from imperfections, an extinction ratio as high as $10^{-10}$ can be readily achieved. Measurements of the emitted light intensity differences between parallel and perpendicularly polarized luminescence with the above resolution allowed our instrument to detect the angle of polarization changes which are even a few orders of magnitude lower than required.

In this instrument we also use a lock-in amplifier synchronized detection for amplification of small electrical signal coming from detectors such as photomultiplieres or photodiodes. These approaches guarantee that small signals of native luminescence from blood can be detected.

It is also our aim to provide a reliable calibration technique for the instrument. Calibration which aims at distinguishing between changes of emitted light polarization due to glucose blood level changes and constant background due to optical activity of other centers in the blood is based on a Glucose Tolerance Test. The test should be performed for every individual patient under medical supervision. During the test the patient orally intakes a certain amount of glucose. Measurements of the patient's blood glucose levels are performed for the period of, for example, two hours after glucose intake at certain intervals by analytical methods and by our instrument. Intervals for analytical methods can be, for example, every 15 minutes and measurements by the described instrument can be performed, for example, every five minutes. Data are collected by an instrument microprocessor. A computer program correlates the calibration value of blood glucose levels with arbitrary units of changes of the ratio of polarization rotation by linear or nonlinear approximations. The advantage of this method of calibration is based on the wide range of blood glucose levels during the Glucose Tolerance Test which can vary between 70 mg/dL up to 400 mg/dL. Such a calibrated instrument can be readily used by a patient.

DESCRIPTION OF THE PREFERRED EMBODIMENT

The present invention is directed at a method, apparatus and procedure for non-invasive detection of the concentration changes of sugar in body liquids, such as blood, using native visible and/or near infrared luminescence.

Figure 1:
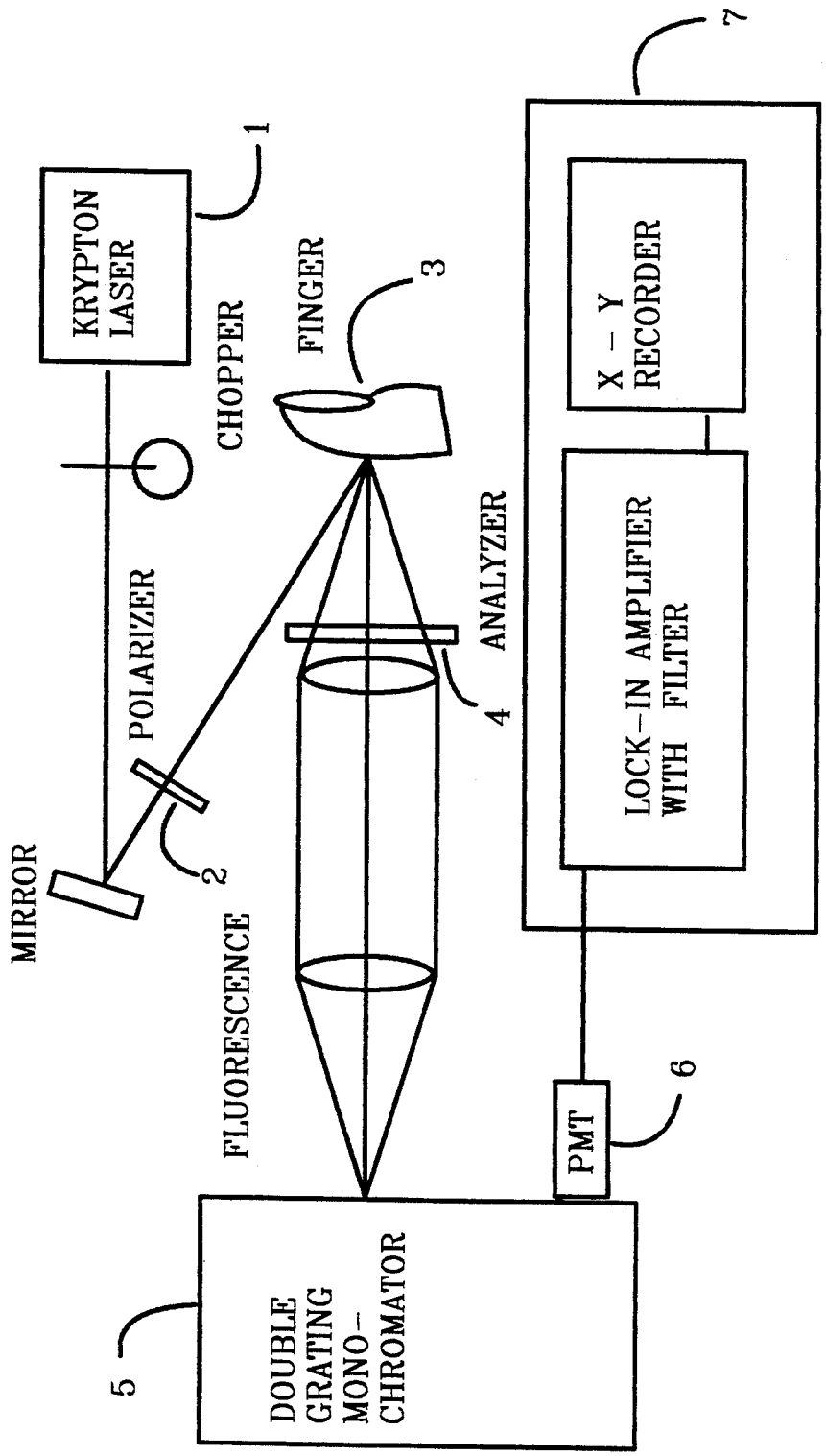
FIG. 1 is a schematic diagram of an experimental setup used to measure luminescence polarization ratio from human tissue.

An experimental arrangement used to measure the polarized luminescence spectra from human tissue is shown in FIG. 1. A Krypton ion laser 1 operating at 647.1 nm was linearly polarized by polarizer 2, and was then directed to the human tissue 3 which in our case was a part of the finger-tip. The native luminescence from the tissue was collected into the double grating monochromator 5 passing first through the polarization analyzer 4 which had its optical axis set parallel or perpendicular to the incident linearly polarized laser light. The photomultiplier tube 6, located at the exit slit of the tunable monochromator 5 measured the intensity at different wavelengths. The output of the PMT 6 was connected to an electronic recording device 7 which included a lock-in amplifier with band-pass filter and X-Y recorder to display each spectrum.

Figure 2:
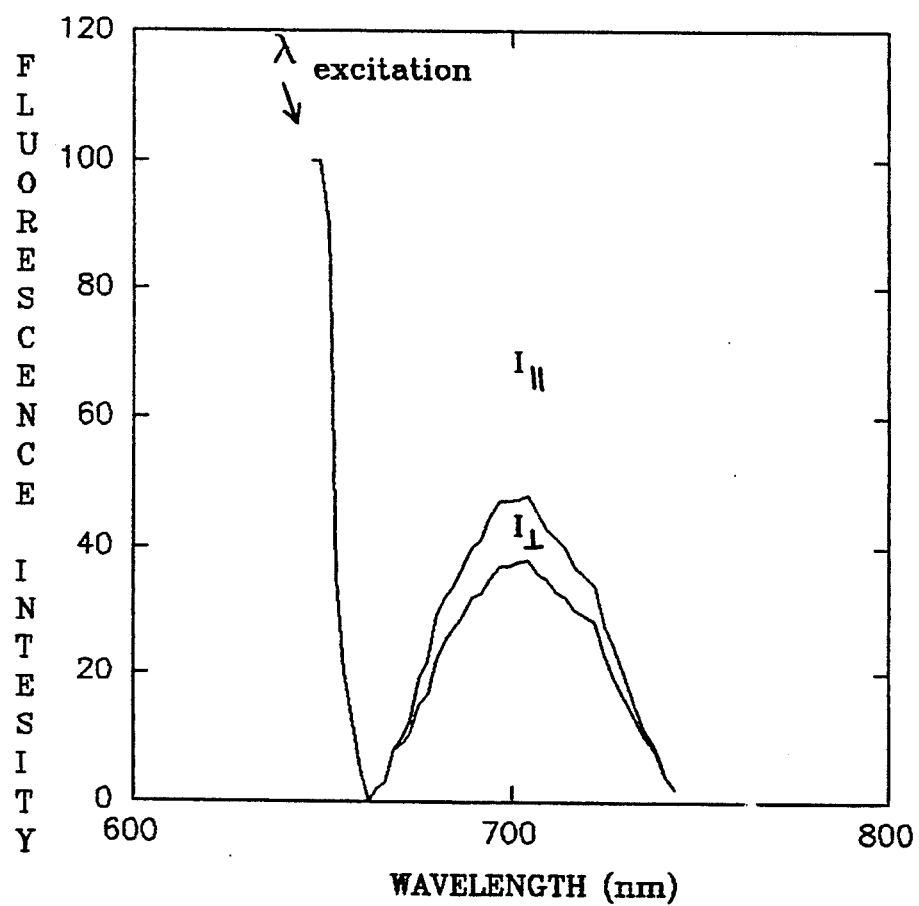
FIG. 2 is a luminescence spectrum of the blood excited by krypton laser at 647.1 nm wavelength.

The luminescence spectra emitted from the blood were investigated. The spectral curves for parallel and perpendicular polarization in respect to the excitation polarization are displayed in FIG. 2. One can readily observe the difference in intensity for parallel and perpendicular polarization of emission from the tissue. Light is preferably absorbed by molecules whose transition moment is parallel to the electric vector of light. Light is also absorbed by molecules whose transition moment is not parallel to the electric vector of light; however, absorption occurs with a reduced probability. The electric vector of the luminescent emission will be polarized in the same plane as the exiting beam if the chromphar is held stationary and is not undergoing other changes. However, molecular motion, energy transfer, the different direction of the emitting dipole as well as the medium through which the emitted photons have to pass through before they exit from tissue will depolarize the emitted beam. The excitation wavelength of krypton laser at 647.1 nm chosen in our experiment does not excite blood in its characteristic absorption band centered at 420 nm. The main reason that this wavelength was selected is that emission from the blood with this excitation centered at about 700 nm which fits to the transparency window of the tissue constituents. It can give a larger number of emitted photons for detection. Other reasons are based on the observation that with a larger gap between excitation and emission wavelengths one can have very small differences between parallel and perpendicular emission from the tissue due to energy transfer processes and other depolarization processes in the chemical constituents in the tissue.

Figure 3:
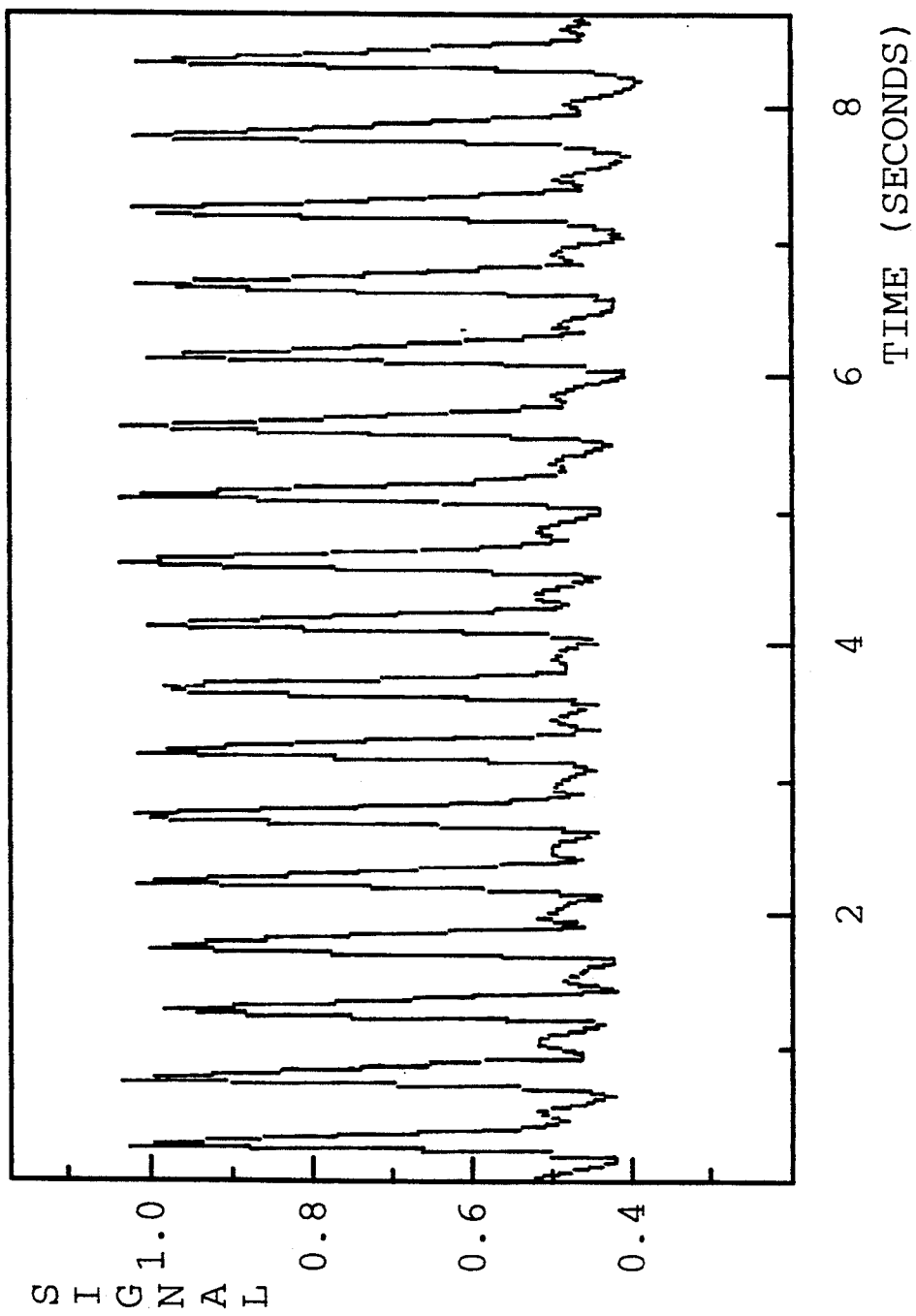
FIG. 3 is a diagram showing the modulation of the luminescence signal in conjunction with the heart rate.

The signal from the lock-in amplifier was passed through a band-pass filter which allowed only frequencies in the range of the heart rate to pass through. FIG.3 shows a typical luminescence signal modulated by motion of the blood in accordance with the heart rate. This signal was then integrated with a time constant much longer than the heart frequency and sent to the X-Y recorder to display each spectrum. The salient feature of the recorded spectra is that the ratio of polarization can be calculated according to the following formula:

$$P(\lambda) = [I_{\|}(\lambda) - I_{\perp}(\lambda)] / [I_{\|}(\lambda) + I_{\perp}(\lambda)],$$

where $\|$ and $\perp$ indicates parallel and perpendicular polarization, respectively; and $\lambda$ indicates the luminescence wavelength. This ratio $P(\lambda)$ which measures the degree of polarization has values in the range $-1$ to $+1$. It is directly proportional to the concentration of optically active constituents of the blood.

The most salient feature of the present invention is that from the polarization ratio of at native luminescence different emission wavelengths from the blood one can determine the concentration of blood sugar. Blood can be excited by different wavelengths not limited to the krypton laser wavelength. For example, as mentioned early, one can excite blood in its characteristic absorption band centered at 420 nm. Emission spectra can be picked at different wavelengths not limited to those presented. The ratio of polarization between parallel and perpendicular luminescence intensity can be measured all over the visible, near infrared and infrared region of the spectrum.

It is another feature of this invention that not only the polarization ratio between parallel and perpendicular polarization of the emitted luminescence can be measured in comparison with a linearly polarized excitation beam. It is another salient feature of this invention that excitation light can be linearly or circularly polarized. Collected emission can also be polarized circularly by applying quarter wave plates in the path of collection optics. This feature is based on the property of the asymmetric molecules like sugar to absorb right-handed circularly polarized light to a different extent than left-handed polarized light. By monitoring the asymmetry of the signal from the emitting molecules, the ratio for circular polarization of luminescence can be calculated according to the following formula:

$$P_c(\lambda) = [I_+(\lambda) - I_-(\lambda)] / [I_+(\lambda) + I_-(\lambda)],$$

where $-$ and $+$ indicates left- and right-handed polarization of light at luminescence wavelength $\lambda$. The ratio $P_c(\lambda)$ provides another coefficient directly proportional to the concentration of the sugar in body liquids.

It is still another salient feature of the presented invention that changes of blood sugar concentration are proportional to changes of the polarization ratio for orthogonally or circularly polarized emission from the chromophores in the blood undergoing interaction with attached to and/or dissolved sugar molecules.

Figure 4:
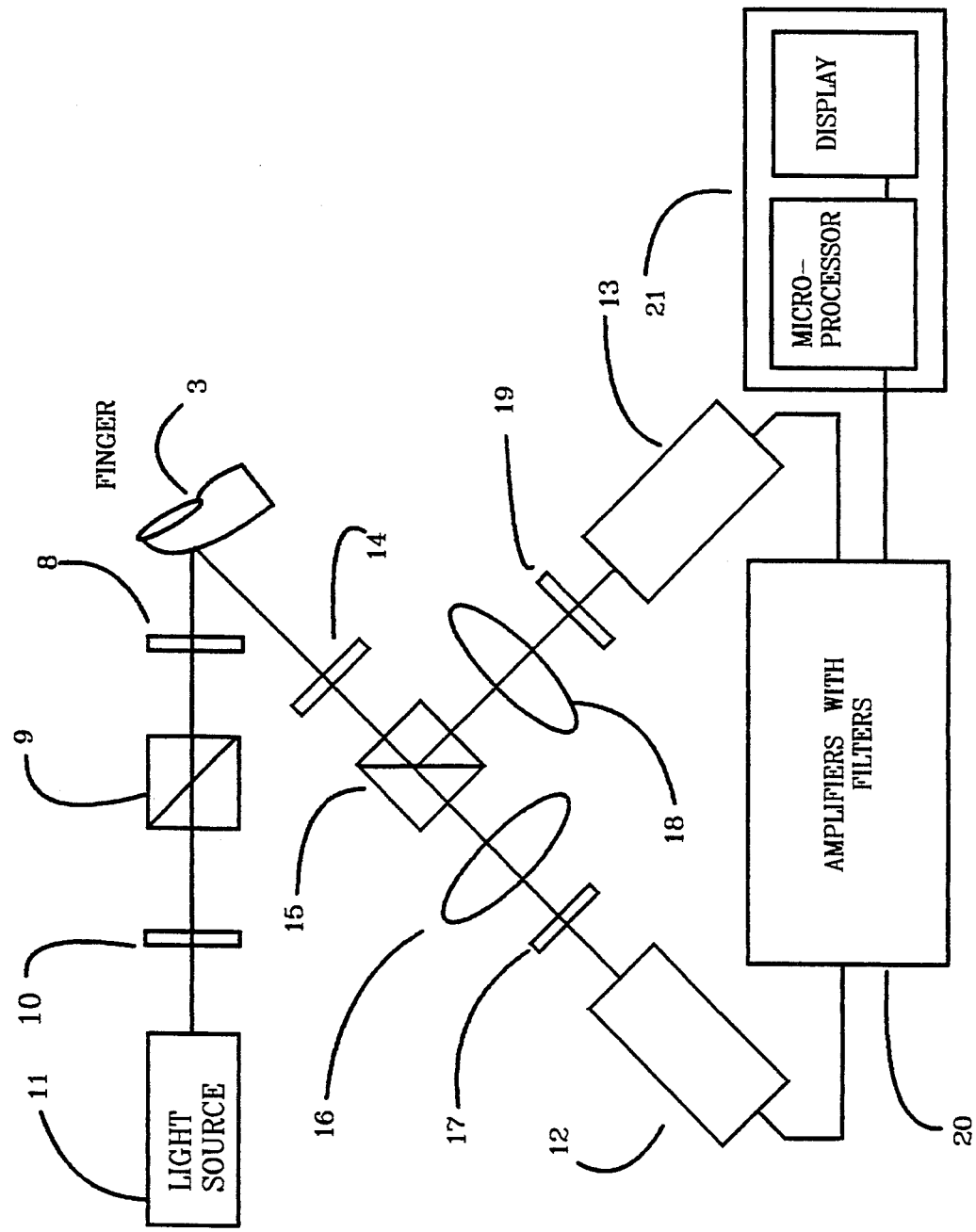
FIG. 4 is a simplified diagram of an embodiment of an apparatus of the invention

In FIG. 4 an embodiment of an apparatus for measuring changes in blood glucose concentration according to the teaching of this invention is illustrated. The apparatus includes a source 11 of light, such as laser, laser diodes, Light Emitting Diodes, or tungsten-halogen filament lamp with a narrow band filter 10 but not limited to it. The light source 11 has power attached to it from a power supply (not shown). Narrow band filter 10 has a bandwidth of less than about 30 nm and preferably less than about 10 nm and is designed to pass light at an excitation wavelength of absorption band of chromophores the blood. Light from source 11 is passed through filter 10 and polarizer 9 which can be any crystal or Polaroid polarizer with a high extinction coefficient. Then optionally for excitation by circular polarization, light is passed through the quarter wave plate 8. Optionally light from source 11 can be focused on the sample tissue but a lens or telescopic system must be positioned before polarizer 9 at the location corresponding to the position of the filter 10. This positioning prevents any depolarization due to optical imperfection in the lenses. Between the sample and polarizer only a quarter wave plate 8 can be introduced. Emitted light from the tissue is collected by another optical system. The main element includes analyzer 15. Between it and the sample only a quarter wave plate 14 can be introduced to prevent any distortion of polarization due to optical imperfection. Polarizer 15 working as an analyzer also has a high extinction coefficient. Collecting lenses 16 and 18 are located behind the analyzer. They collect luminescence light from the sample and focus it on the photocatode of photomultiplieres 12 and 13 or photodiodes 12 and 13 depending on the amount of the emitted luminescence photons from the tissue. In front of both light detectors 12 and 13 narrow band or color filters are placed to select emitted wavelength of luminescence. Analyzer 15 which can be a calcite Clan Prism is dividing emitted luminescence into two paths. Each path contains perpendicularly polarized or left- and right-handed polarized luminescence from the tissue. Polarizer 9 can be oriented along one of the polarization axis of analyzer 15 or can be oriented at 45° or another angle in comparison with analyzer 15. The electrical signals from the photodetectors 12 and 13 are passed to amplifier 20 which can be a lock-in amplifier with filter for the heart beat frequencies or can be an amplifier integrated circuit with said filter. An amplified electrical signal is then passed to the computer system 21 which can include a microprocessor and a software and display system but is not only limited to it. This unit 21 also has an important role during the calibration procedure for calculating and storing information. It will process data during the Glucose Tolerance Test, linearize them with measurements from our instrument and a conventional blood glucose level measuring apparatus. The display unit of the instrument will have a crucial role during the day-to-day operation and will display concentration of blood glucose for every measurement in diabetic patients. A computer may also store information for keeping records of the measurement of the patient's blood glucose levels.

The embodiments of the present invention are intended to be merely exemplary and those skilled in the art shall be able to make numerous variations and modifications to it without departing from the spirit of the present inventions. All such variations and modifications are intended to be within the scope of the present invention as defined in the appended claims.

What is claimed is:

1. A method of determining blood glucose concentration from non-invasive measurements of a state of polarization of light emitted by a luminescing center of blood which are dissolved and/or attached to optically active molecules of sugar and upon interaction rotate the initial polarization comprising:
   a. illuminating sample tissue with a beam with linearly or circularly polarized light,
   b. said light having a wavelength absorbed by blood constituents,
   c. detecting emitted luminescence light from the tissue at a predetermined emission wavelength,
   d. analyzing the state of polarization of said emitted light,
   e. correlating the state of emitted light polarization with blood glucose concentration.

2. An instrument for non-invasive blood glucose measurements based on a state of polarization of native luminescence from blood comprising:
   a. means for illuminating a blood carrying tissue with a beam of monochromatic, polarized light, and causing the blood in said tissue to emit native luminescence light,
   b. means for detecting said emitted native luminescence light from the blood at a predetermined wavelength,
   c. means for detecting the state of polarization of the emitted native luminescence light from the blood, and
   d. means for correlating the polarization state of the emitted native luminescence light from said blood with blood glucose concentration.

3. The instrument of claim 2, wherein the illuminating means includes light source means for emitting a beam of light, polarizing means for polarizing the emitted light, and focusing means for focusing the polarized light on said blood carrying tissue.

4. The instrument of claim 3, wherein the light source means is selected from the group consisting of lasers, light emitting diodes, and lamp light sources.

5. The instrument of claim 2, wherein the detecting means comprises analyzing means for receiving the emitted native luminescence light from the blood, photodetector means for detecting the received native luminescence light from said analyzing means and producing an output signal, focusing means for focusing the received native luminescence light on the photodetector means, and wavelength selecting means for allowing only wavelengths of the emitted native luminescence light to reach the photodetector means.

6. The instrument of claim 5, wherein the photodetector means is selected from the group consisting of photodiodes and photomultipliers.

7. The instrument of claim 2, wherein the detecting means comprises filter means for filtering the output signal from the photodetector means for allowing only signals at a heart rate frequency to pass and amplification means for amplifying the passed signals at the heart rate frequency.

8. The instrument of claim 7, wherein the amplification means is an electronic amplifier.

* * * * *